United States Patent
van West et al.

(10) Patent No.: US 9,139,824 B2
(45) Date of Patent: Sep. 22, 2015

(54) *SAPOLEGINA* PROTEIN IN FOR USE AS A MEDICAMENT

(75) Inventors: Pieter van West, Aberdeen (GB); Christopher John Secombes, Aberdeen (GB); Victoria Louise Anderson, Aberdeen (GB); Kirsty Louise Minor, Aberdeen (GB)

(73) Assignee: The University Court of the University of Aberdeen, Aberdeen (GB)

( * ) Notice: Subject to any disclaimer, the term of this patent is extended or adjusted under 35 U.S.C. 154(b) by 0 days.

(21) Appl. No.: 14/112,388

(22) PCT Filed: Apr. 20, 2012

(86) PCT No.: PCT/EP2012/057233
§ 371 (c)(1),
(2), (4) Date: Oct. 17, 2013

(87) PCT Pub. No.: WO2012/143488
PCT Pub. Date: Oct. 26, 2012

(65) Prior Publication Data
US 2014/0037664 A1 Feb. 6, 2014

Related U.S. Application Data

(60) Provisional application No. 61/477,794, filed on Apr. 21, 2011.

(30) Foreign Application Priority Data

Apr. 21, 2011 (EP) .................................... 11163370

(51) Int. Cl.
| | |
|---|---|
| A61K 39/00 | (2006.01) |
| A61K 39/295 | (2006.01) |
| A61K 38/43 | (2006.01) |
| A01N 63/00 | (2006.01) |
| A61K 48/00 | (2006.01) |
| A61K 45/00 | (2006.01) |
| C12N 9/00 | (2006.01) |
| C12N 1/00 | (2006.01) |
| C12N 9/58 | (2006.01) |
| A61K 38/48 | (2006.01) |
| C12N 9/50 | (2006.01) |
| C07K 16/40 | (2006.01) |

(52) U.S. Cl.
CPC ................ *C12N 9/58* (2013.01); *A61K 38/482* (2013.01); *A61K 39/0002* (2013.01); *C07K 16/40* (2013.01); *C12N 9/50* (2013.01)

(58) Field of Classification Search
None
See application file for complete search history.

(56) References Cited

FOREIGN PATENT DOCUMENTS

WO 88/09668 A1 12/1988

OTHER PUBLICATIONS

Leveque et al., "Global diversity of fish (Pisces) in freshwater," Hydrobiologia 595: 545-567 (2008).*
Rudikoff et al., "Single amino acid substitution altering binding specificity," PNAS 79: 1979-1983 (1982).*
Ng et al., "SIFT: predicting amino acid changes that affect protein function," Nucleic Acids Research: vol. 31, No. 13,: 812-3814 (2003).*
Rock et al., "Natural endogenous adjuvants," Springer Semin Immun 26: 231-246 (2005).*
Mayer et al., "Saprolegnia: There's a fungus among us," Jun. 1, 2005, Retrieved from the Internet: < URL:http://hmsc.oregonstate.edu/classes/MB492/saprokent/saprolegnia.htm>.*
Gieseker et al., "Formalin treatment to reduce mortality associated with *Saprolegnia parasitica* in rainbow trout, Oncorhynchus mykiss", Aquaculture, 2006, pp. 120-129, vol. 253.
Fregeneda-Grandes et al., "Antibody response of brown trout Salmo trutta injected with pathogenic *Saprolegnia parasitica* antigenic extracts", 2007, pp. 107-111, vol. 74.
Fregeneda-Grandes et al., "Prevalence of serum antibodies against *Saprolegnia parasitica* in wild and farmed brown trout Salmo trutta", Diseases of Aquatic Organisms, 2009, pp. 17-22, vol. 83.
Hodkinson et al., "Immune response of U.D.N.-infected salmon to *Saprolegnia*", J. Fish Biol., 1970, pp. 305-311, vol. 2.
Phillips et al., "New insights into animal pathogenic oomycetes", Trends in Microbiology, 2007, pp. 13-19, vol. 16(1).
Torto-Alalibo et al., "Expressed sequence tags from the oomycete fish pathogen *Saprolegnia parasitica* reveal putative virulence factors", BMC Microbiology, 2005, pp. 1-13, vol. 5(1).
Database EMBL [Online], "MC21-C03-T396 Cablnf Cabomba aquatica cDNA, MRNA sequence", Oct. 14, 2010, Accession No. H0771558, XP-002657510, Abstract.
European Search Report for Application No. EP 11 16 3370, mailed on Sep. 6, 2011.
International Search Report for corresponding PCT/EP2012/057233, mailed on Jun. 13, 2012.
Lipman, et al., Rapid and Sensitive Protein Similarity Searches, Science, 1985, pp. 1435-1441, vol. 227.
Minor, et al., A putative serine protease, SpSsp1, from *Saprolegnia parasitica* is recognised by sera of rainbow trout, Oncorhynchus mykiss, Fungal Biology, 2014, pp. 630-639.

* cited by examiner

*Primary Examiner* — Zachariah Lucas
*Assistant Examiner* — M. Franco Salvoza

(57) ABSTRACT

The present invention pertains to a protein having the characteristics of a serine protease having an amino acid sequence according to SEQ ID NO 2 for use as a medicament. The invention also pertains to this protein for use in a vaccine to protect an animal against an infection with a micro organism that secretes said protein, and to the corresponding antibodies directed against the protein.

13 Claims, No Drawings

SEQUENCE LISTING

```
<160> NUMBER OF SEQ ID NOS: 2

<210> SEQ ID NO 1
<211> LENGTH: 1446
<212> TYPE: DNA
<213> ORGANISM: Saprolegnia

<400> SEQUENCE: 1
atgaaggctg ccatgatcac gctcctcgcc gccgcggccg tcgcccaggc caaggtcgcc      60
agctccgtcc tccgcgacct cgaggtccag ggcgcctcgg acctctacat cacgttcgac     120
cacgtctacc cggtcctccg cgcgctcccc gagtcgaacg acccgagcgt tgtccgtgag     180
gcgcttgtga cccacgcgac gtcgacgcag acggaggcgc ttgccgtcct cggtggcctc     240
gatgcgcagt cgttctggat caccaactcg gtggtcgtca agggtgcgtc ggcggatgtc     300
gtcaacaagc tcaaggcgct caagaacgtc aagaccgtcg accagctccc ggtcgtgacg     360
gtcccggagg tcattatcgg cgagacgggc aagaaccccg aggcgaccaa cgagtggggt     420
gtcgacacgg tcggtgcccc caaggtgtgg cccacgacca acggcaaggg cgcggtcatc     480
ggctcgatcg acacgggcgc cttccacacg cacgagtcca tcaagagcag ctggcgctcg     540
gacaagggct ggtttgatgc tttcaagaag tcggtcaact cgcctgccga tatcgacggc     600
catggcacgc acacgatcgg cacgatggcc ggctccaacg gcattggtgt ggctccgggc     660
gcccagtgga tcgcttgccg cggtctcatc aacggctcgg gttcggccga ctcgctcctt     720
gcctgcgcgc agttcatgct ttgccccacc gacccggatg ggaagaacgc cgactgcaag     780
aaggcgccgc atgtcgtcaa caactcgtgg ggcggctcga gcacggacac gtggttccac     840
ccggctgccc aggcctgggt caaggccggc atcatccccg tcttctccaa cggcaactcg     900
ggcccggcct gctccacgac gggcaacccc ggtttccttg acaacgtcat ctcggtcggc     960
gcgctcggct cgtggacgac ggacagcccc aacgacctcg ccttcttctc gtccaagggc    1020
cccaccaagt acacgggcgc tgacggcaag ccgcgcaacc tcgtcaagcc tgatatcgcc    1080 gccccggct tcttcacgcg ctcggctggc atcaaggcca cgaacgaata cgtcaagatg    1140
gccggtacgt cgatggctgg ccccacgtc gccggtgtcg tcggtctcct caagagcgcc    1200
aaggccgact tgacgtacga ggaagtgtac gcctacgtca ccaagtacgc ctacaccaag    1260
acgttgacgc ccgagccggc cacgtgggtc ggcaaggcca acgcgacgct cccgggcgca    1320
cccaactgcg gcggtgtctc ggacgcctcg ttccccaaca accgctacgg tttcggtcgc    1380
gtcgatgtcg ccaacatgtt tgaaggtggc aagctcaagc cggtcaaccc caaccctgcc    1440
tgctaa                                                                1446

<210> SEQ ID NO 2
<211> LENGTH: 481
<212> TYPE: PRT
<213> ORGANISM: Saprolegnia

<400> SEQUENCE: 2

Met Lys Ala Ala Met Ile Thr Leu Leu Ala Ala Ala Ala Val Ala Gln
1               5                   10                  15

Ala Lys Val Ala Ser Ser Val Leu Arg Asp Leu Glu Val Gln Gly Ala
            20                  25                  30
```

-continued

Ser Asp Leu Tyr Ile Thr Phe Asp His Val Tyr Pro Val Leu Arg Ala
            35                  40                  45

Leu Pro Glu Ser Asn Asp Pro Ser Val Val Arg Glu Ala Leu Val Thr
 50                  55                  60

His Ala Thr Ser Thr Gln Thr Glu Ala Leu Ala Val Leu Gly Gly Leu
 65                  70                  75                  80

Asp Ala Gln Ser Phe Trp Ile Thr Asn Ser Val Val Lys Gly Ala
            85                  90                  95

Ser Ala Asp Val Val Asn Lys Leu Lys Ala Leu Lys Asn Val Lys Thr
                100                 105                 110

Val Asp Gln Leu Pro Val Val Thr Val Pro Glu Val Ile Ile Gly Glu
                115                 120                 125

Thr Gly Lys Asn Pro Glu Ala Thr Asn Glu Trp Gly Val Asp Thr Val
130                 135                 140

Gly Ala Pro Lys Val Trp Pro Thr Thr Asn Gly Lys Gly Ala Val Ile
145                 150                 155                 160

Gly Ser Ile Asp Thr Gly Ala Phe His Thr His Glu Ser Ile Lys Ser
                165                 170                 175

Ser Trp Arg Ser Asp Lys Gly Trp Phe Asp Ala Phe Lys Lys Ser Val
            180                 185                 190

Asn Ser Pro Ala Asp Ile Asp Gly His Gly Thr His Thr Ile Gly Thr
            195                 200                 205

Met Ala Gly Ser Asn Gly Ile Gly Val Ala Pro Gly Ala Gln Trp Ile
    210                 215                 220

Ala Cys Arg Gly Leu Ile Asn Gly Ser Gly Ser Ala Asp Ser Leu Leu
225                 230                 235                 240

Ala Cys Ala Gln Phe Met Leu Cys Pro Thr Asp Pro Asp Gly Lys Asn
                245                 250                 255

Ala Asp Cys Lys Lys Ala Pro His Val Val Asn Asn Ser Trp Gly Gly
            260                 265                 270

Ser Ser Thr Asp Thr Trp Phe His Pro Ala Ala Gln Ala Trp Val Lys
            275                 280                 285

Ala Gly Ile Ile Pro Val Phe Ser Asn Gly Asn Ser Gly Pro Ala Cys
    290                 295                 300

Ser Thr Thr Gly Asn Pro Gly Phe Leu Asp Asn Val Ile Ser Val Gly
305                 310                 315                 320

Ala Leu Gly Ser Trp Thr Thr Asp Ser Pro Asn Asp Leu Ala Phe Phe
            325                 330                 335

Ser Ser Lys Gly Pro Thr Lys Tyr Thr Gly Ala Asp Gly Lys Pro Arg
            340                 345                 350

Asn Leu Val Lys Pro Asp Ile Ala Ala Pro Gly Phe Phe Thr Arg Ser
            355                 360                 365

Ala Gly Ile Lys Ala Thr Asn Glu Tyr Val Lys Met Ala Gly Thr Ser
    370                 375                 380

Met Ala Gly Pro His Val Ala Gly Val Val Gly Leu Leu Lys Ser Ala
385                 390                 395                 400

Lys Ala Asp Leu Thr Tyr Glu Glu Val Tyr Ala Tyr Val Thr Lys Tyr
                405                 410                 415

Ala Tyr Thr Lys Thr Leu Thr Pro Glu Pro Ala Thr Trp Val Gly Lys
            420                 425                 430

Ala Asn Ala Thr Leu Pro Gly Ala Pro Asn Cys Gly Gly Val Ser Asp
            435                 440                 445

```
Ala Ser Phe Pro Asn Asn Arg Tyr Gly Phe Gly Arg Val Asp Val Ala
    450                 455                 460

Asn Met Phe Glu Gly Gly Lys Leu Lys Pro Val Asn Pro Asn Pro Ala
465                 470                 475                 480

Cys
```

SAPOLEGINA PROTEIN IN FOR USE AS A MEDICAMENT

CROSS-REFERENCE TO RELATED APPLICATIONS

This application is a national stage entry under 35 U.S.C. §371 of PCT/EP2012/057233, filed on Apr. 20, 2012, which claims priority to U.S. Provisional Application No. 61/477,794, filed on Apr. 21, 2011, and EP Application No. 11163370.7, filed on Apr. 21, 2011. The content of PCT/EP2012/057233 is hereby incorporated by reference in its entirety.

The present invention pertains to a protein for use as a medicament. In particular, the invention pertains to a subtilisin-like serine protease which corresponds to protection against an infection with a micro-organism which secrets such a serine-protease.

Some of the most devastating infections on fish in aquaculture are caused by oomycetes, including *Saprolegnia*, *Achlya* and *Aphanomyces* species. *Saprolegnia parasitica* is endemic to all fresh water habitats and is believed to be responsible, in part, for the decline of natural populations of salmonids globally. Saprolegniosis, the disease caused by *Saprolegnia* species, is characterised by grey or white fluffy patches of mycelia visible on the surface of the fish, particularly around the head, tail and fins. Infection is primarily of epidermal tissue and can, in extreme cases, cover the entire body of the host. Tissue containing lesions may appear supple and ulcerated, potentially with necrotic regions, while the surrounding areas can demonstrate fluid retention and cell death. It has been speculated that fish infected by *S. parasitica* die from haemodilution as a result of weakened defences provided by the epidermis following penetration by mycelia.

Aquaculture is one of the world's fastest-growing food sectors, currently accounting for more than 30% of total fish production with a large proportion of this coming from freshwater aquaculture. Within the aquaculture industry, oomycete and fungal infections cause substantial economic losses, second only to bacterial diseases. *Saprolegnia* species are responsible for these oomycete infections, affecting approximately 1 in 10 hatched salmon raised in fish farms.

For many years, saprolegniosis was kept under control through the use of the organic dye malachite green. However, following a ban on the use of malachite green on food fish in 2002 due to potential carcinogenic effects, saprolegniosis is once more prominent in aquaculture. The addition of salt (NaCl) to tank water is believed to be effective in controlling saprolegniosis. However, it does not totally prevent growth of *Saprolegnia* species, nor is it considered a viable alternative to malachite green due to the large quantities that would be required in aquaculture. At present, formalin is used to control saprolegniosis, however it's use is currently under review due to environmental, health and work safety considerations (EU Biocide Product Directive 2009). It is therefore clear that alternatives must be sought for the control of *S. parasitica*.

It is an object of the present invention to arrive at a medicament that can be used to treat an infection with pathogenic micro organisms whose virulence involves the secretion of a serine protease, such as for example Oomycetes, in particular *Saprolegnia* species.

To this end it was found that a protein having the characteristics of the serine protease having an amino acid sequence according to SEQ ID NO 2 can be used as a medicament, for example to prevent an infection with pathogenic micro-organisms, such as *Saprolegnia parasitica*, that secret such serine proteases. Next to this protein, the invention also pertains to the use of this protein in a vaccine, the vaccine itself, isolated DNA that corresponds to the protein, the use of this DNA in a vaccine, and antibodies against the protein.

The present invention was based on the finding that animals (which term includes humans) having antibodies against the current protein, are protected (which term includes partial protection) against an infection with the pathogenic micro organism that secrets the protein. In particular it was found in an initial Ami-momi infection experiment of rainbow trout (see i.a. in "Characteristics of two *Saprolegnia* species isolated from Coho salmon with saprolegnosis", Journal of Aquatic Animal Health, 5: 115-118, 1993, Hatai et al; and in "Morphological and physiological characteristics of *Saprolegnia* spp. strains pathogenic to Atlantic salmon, *Salmo salar*", L. Journal of Fish Diseases 28:445-453, 2005, Stueland et al.) that several fish did not become infected upon challenge with wild-type *Saprolegnia parasitica*. Pre-immune sera of challenged and non-challenged fish was isolated and it was surprisingly found that only one out of the many secreted *Saprolegnia parasitica* protein was recognised by the pre-immune sera of these fish. It is believed that the fish had been in contact with *Saprolegnia* before they were challenged. The said secreted protein appears to be a subtilisin-like serine protease. Given the fact that this was the only protein that was found to be recognized by the pre-immune sera, it is believed that the immune response against this protein is involved in protection of the fish against wild type *Saprolegnia parasitica*. On its turn, the protein could thus serve as a medicament to evoke the required immune response to treat (i.e. to prevent, mitigate or cure) an infection with the corresponding micro organism that secrets this protein.

Indeed, it has been suggested in the art that serine proteases may act as a virulence factor. However many pathogenic micro-organisms typically express multiple serine proteases, each of which are believed to be at best only partially involved in virulence. Even *Saprolegnia parasitica* expresses an estimated number of 50-60 serine proteases. It was now surprisingly found that the immune response against one specific serine proteases out of the many present, is dominantly involved in protection against the corresponding micro organism. Applicant also recognized that a protein having the characteristics of the found serine protease according to SEQ ID NO 2 is produced by many pathogenic micro-organisms. It is thus believed that an immune response against this protein will lead to (at least partial) protection against the corresponding micro organism which secrets this protein. In this respect it is noted that the characteristics of the serine protease according to SEQ ID NO 2 are 1) the fact that it is a serine protease, 2) the fact that it has a conserved subtilisin domain, viz. the Peptidase S8/S53 superfamiliy domain with a conserved Asp/His/Ser catalytic triad (amino acids 164, 201 and 384 in SED ID NO 2 respectively), 3) that it is secreted and 4) that an immune response against the protein corresponds to (at least partial) protection against the micro organisms. With regard to the fourth characteristic, a protein according to the invention thus at least has to have the relevant immunogenic epitope(s) of the serine protease according to SEQ ID NO 2, i.e. the epitope(s) that correspond to the protective antibodies found in the fish as described supra.

A protein having the relevant immunogenic epitope(s) of the serine protease according to SEQ ID NO 2 can be found i.a. by three dimensional structure predictions as is commonly applied in the art. When a secreted subtilisin-like serine protease appears to have a similar 3D structure containing structurally conserved domains (SCRs) in comparison to SEQ ID NO 2, the relevant immunogenic epitope(s) are with a high degree of certainty present, even if the overall sequence similarity is less than for example 50%.

A useful and fast method for 3D structure prediction is homology modeling of proteins based on sequence homology. The approach is based on the fact that related proteins within a protein family that have a high degree of amino acid sequence similarity also have similar protein folds. Proteins for which the 3D structure is already known serve as reference proteins or templates. First, the amino acid sequence of the protein to be modeled is compared with the sequence of the reference protein(s) using pair wise or multiple sequence alignments (in case of several reference proteins). For sequences with identities of more than 70%, the modeled structures can be predicted very accurately. For sequences with identities between 30% and 70% the structures can be predicted with fair accuracy. However, for sequences with identities of less than 30%, difficulties with the modeling generally arise. The sequence identities of structurally conserved regions (SCRs) are frequently above those of less conserved loops and both influence the degree of identity of the complete sequence. To identify SCRs in the reference proteins, a structural alignment of the amino acid sequences based on the secondary structure is performed. The sequence to be modeled is then arranged onto the oriented templates and the spatial coordinates of the SCRs are then transferred to the model sequence. The coordinates of the loops are usually taken from similar regions of other protein structures. The spatial orientation of the side chains of individual amino acids in the SCRs is maintained as in the templates. For all nonconserved side chains, the statistically most likely position is taken. The process of homology modeling is completed both by calculations that lead to energy minimization of the model and checking of the structural relevance of the resulting protein model. Such 3D modeling is commonly applied in the art of protein science and its application is for example described by Holm et al. in *Nucleic Acids Research*, 2010, Vol. 38, Web Server Issuea, W545-W549; by Dunbrack Jr in *Current Opinion in Structural Biology*, 2006, 16:374-384; by Kolodny et al. in *Current Opinion in Structural Biology*, 2006, 16:393-398; by Zhang in *Current Opinion in Structural Biology*, 2008, 18:342-348 and in *Current Opinion in Structural Biology*, 2009, 19:145-155.

Alternatively, the presence of the relevant immunogenic epitope(s) can be established experimentally. When a secreted subtilisin-like serine protease has been identified (thus having three of the four characteristics of the serine protease according to SEQ ID NO 2), and its amino acids sequence is identical with the sequence according to SEQ ID NO 2 for 70% or more over its full length, or for example 80-90% over a length of at least 30-50 amino acids amino acids, the serine protease can be tested with regard to the presence of the relevant immunogenic epitope(s) corresponding to the present invention for example by assessing reaction with the antibodies present in animals that are protected against an infection with the micro-organism, or by assessing whether animals can be (at least partially) protected against such an infection by using the protein as a vaccine antigen, or by assessing cross reaction with the antigens as found in the pre-immune sera of fish protected against *Saprolegnia parasitica*. It is noted that fish protected against *Saprolegnia parasitica* can be found easily in the wild since it has been known for long time for example that almost all wild salmon have been infected with this pathogen (about 93%), but only 66% actually demonstrate signs of saprolegniosis (Hodkinson et al: "Immune response of U.D.N.-infected salmon to *Saprolegnia*", in the Journal of Fish Biology 2: 305-311, 1970).

Indeed when a secreted subtilisin-like serine protease has the relevant immunogenic epitope(s) as present in the serine protease according to SEQ ID NO 2, it is a protein according to the present invention although the overall identity of the amino acids sequence may be even as low as for example 40%. Also, a polypeptide that incorporates the relevant immunogenic epitope(s) of the serine protease according to SEQ ID NO 2 is a protein for use according to the invention, even if it does not have the full length of the serine protease according to SEQ ID NO 2. Indeed, it is commonly known that when a protein is used for e.g. vaccination purposes or for raising antibodies, it is not necessary to use the full length protein. It is also possible to use a part of that protein that incorporates the relevant immunogenic epitope(s) and thus is capable, as such or coupled to a carrier such as e.g. KLH (keyhole limpet hemocyanin), of inducing an adequate immune response against the full length protein. Such a part is also referred to as an "immunogenic fragment". A variety of techniques is available to easily identify such immunogenic fragments as indicated here-above. Anther method is for example the PEPSCAN method as described by Geysen et al (Patent Application WO 84/03564, Patent Application WO 86/06487, U.S. Pat. No. 4,833,092, Proc. Natl Acad. Sci. 81: 3998-4002 (1984), J. Imm. Meth. 102, 259-274 (1987). This method is an easy to perform, quick and well-established method for the detection of relevant immunogenic epitopes. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47: 45-148 (1987) and U.S. Pat. No. 4,554,101). T-cell epitopes can likewise be predicted from the sequence by computer with the aid of Berzofsky's amphiphilicity criterion (Science 235, 1059-1062 (1987) and U.S. patent application Ser. No. NTIS 07/005,885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzowsky for HIV-epitopes; The FASEB Journal 5:2412-2418 (1991).

Still, in a preferred embodiment the protein is a full length protein (corresponding to the DNA from start codon to stop codon). The native three dimensional presentation of the full-length protein is preferred, in order to arrive at an adequate immune response to prevent an infection with the corresponding micro organism.

It will be understood that natural variations do exist between the serine proteases for use according to the present invention, as secreted by several distinct micro organisms. These variations may be demonstrated by (an) amino acid difference(s) in the overall sequence or by deletions, substitutions, insertions, inversions or additions of (an) amino acid (s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting proteins retain their immune reactivity.

Preferably a protein according to the present invention has an amino acid sequence that is at least 70% identical to SEQ ID NO 2. More preferably, the protein has an amino acid sequence that is at least 90% identical to SEQ ID NO 2, or even 92%, 94%, 96%, 98% or even 100%. Having such identity levels, although being isolated from various different species of micro organisms might explain why the protein may induce a corresponding immunological response.

The level of protein homology can be determined with the computer program "BLAST 2 SEQUENCES" by selecting sub-program: "BLASTP", which is referred to in Tatiana A. Tatusova, Thomas L. Madden FEMS Microbiol. Letters 174: 247-250 (1999). Matrix used: "blosum62". Parameters used are the default parameters (Open gap: 11. Extension gap: 1. Gap x_dropoff: 50).

As indicated supra, the present invention also pertains to a protein having the characteristics of the serine protease according to SEQ ID NO 2 for use in a vaccine to protect an animal against an infection with a micro organism that secrets said protein. Applicant found that in fish that could not be infected with *Saprolegnia parasitica*, the sole immune response detected against a mixture of all secreted *Saprolegnia* proteins was a response against this particular subtilisin-like serine protease This inherently means that with this serine-protease it is possible to evoke an adequate, protective, immune response. As is commonly known, an adequate immune response against a protein can be evoked using an adjuvant, or by having the protein expressed in the host itself using a live recombinant carrier such as a virus (or virus like particle) or a bacterium. In this respect it is noted that a vaccine in the sense of this invention is a constitution suitable for application to an animal, comprising one or more antigens, typically combined with a pharmaceutically acceptable carrier such as a liquid based on (optionally buffered) water, which upon administration to the animal induces an immune response for treating an infection with a pathogenic micro organism, i.e. aiding in preventing, ameliorating or curing the said infection. In general, a vaccine can be manufactured by using art-known methods that basically comprise admixing the antigens (or a composition containing the antigens) with the pharmaceutically acceptable carrier. In the vaccine, the antigens are present in an immunologically effective amount, i.e. in an amount capable of stimulating the immune system of the target animal sufficiently to at least reduce the negative effects of a challenge with the wild-type micro-organisms. Optionally other substances such as adjuvants, stabilisers, viscosity modifiers or other components are added depending on the intended use or required properties of the vaccine. An adjuvant is in general not needed to obtain an immune response but is able to favor or amplify one or more particular processes in the cascade of immunological events, ultimately leading to a better immunological response. Hence, the presence of an adjuvant, in particular when using a non-live vaccine may increase the chance of evoking an adequate immune response in a target animal.

In an embodiment, the protein is for use in a vaccine to protect an animal against an infection with Oomycetes. The Oomycetes or water moulds are a class of organisms that is part of the Chromalveolate "superkingdom" clade. They comprise a group of heterotropic, fungus-like organisms that are related to the heterokont algae. They are distinguished from true fungi by the presence of biflagellate zoospores. Oomycetes are cosmopolitan, occurring in fresh and salt water, in soil, and as terrestrial parasites of plants. Vaccines against Oomycetes are not commercially available. The present invention enables the provision of a vaccine to treat an infection with Oomycetes in animals.

In a further embodiment, the protein is for use in a vaccine to protect an animal against *Saprolegnia* species. *Saprolegnia* species, like many water moulds, are thought to be both saprotrophitic and necrotrophtic. Typically feeding on waste from fish or other dead cells, they will also take advantage of animals that have been injured or of compromised eggs. When they inhabit a live animal, they exhibit as a fungal infection known as mycoses. *Saprolegnia* species are generally secondary pathogens, though in the right circumstances, they may act as primary pathogen. It most frequently targets fish, both in the wild and in tank environments. Through cellular necrosis and other epidermal damage, *Saprolegnia* species will spread across the surface of its host as a cotton-like film. A *Saprolegnia* infection is usually fatal, eventually causing haemodilution, though the time to death varies depending on the initial site of the infection, rate of growth and the ability of the organism to withstand the stress of the infection. The present invention enables the provision of a vaccine to treat an infection with *Saprolegnia* species in animals.

In yet a further embodiment, the protein is for use in a vaccine to protect an animal against *Saprolegnia parasitica*, the pathogen described supra.

In an embodiment, the vaccine comprises next to the current protein, antigens of one or more of the micro organisms *Aeromonas salmonicida, Yersinia ruckeri, Flavobacterium columnarae, Flavobacterium psychrophilum, Vibrio ordalii, Vibrio anguillarum, Vibrio salmonicida, Moritella viscose*, infectious pancreatic necrosis virus (IPNV), salmonid alphavirus (SAV), infectious hematopoietic necrosis virus IHNV), viral haemorrhagic septicaemia virus (VHSV) and infectious salmon anaemia virus (ISAV).

The invention also pertains to isolated DNA (i.e. DNA taken out of its native chromosome) having the characteristics of the DNA according to SEQ ID NO 1 for use as a medicament. To be able and serve as a medicament (for example a vaccine that protects against an infection with a micro-organism that secrets a protein corresponding to the present invention), the DNA could be used to in vivo express the corresponding protein that evokes the protective immune response against the corresponding pathogenic micro organism. This could be done in the form of a live recombinant carrier (LRC) comprising the DNA, or alternatively, the DNA could be used as such in a so called DNA vaccine. Preferably, the invention is embodied in a live recombinant carrier (comprising a nucleic acid encoding the protein according to the invention. The carrier could be e.g. a bacterium or virus. Animals infected with such LRCs will produce an immunogenic response not only against the immunogens of the carrier, but also against the immunogenic parts of the protein(s) for which the genetic code is additionally cloned into the LRC. As an example of bacterial LRCs, attenuated *Salmonella* strains known in the art can attractively be used. Live recombinant carrier parasites have i.a. been described by Vermeulen, A. N. (Int. Journ. Parasitol. 28: 1121-1130 (1998)).

Also, LRC viruses may be used as a way of transporting the nucleic acid into a target cell. Live recombinant carrier viruses are also called vector viruses. Viruses often used as vectors are Vaccinia viruses (Panicali et al; Proc. Natl. Acad. Sci. USA, 79: 4927 (1982), Herpesviruses (E.P.A. 0473210A2), and Retroviruses (Valerio, D. et al; in Baum, S. J., Dicke, K. A., Lotzova, E. and Pluznik, D. H. (Eds.), Experimental Haematology today—1988. Springer Verlag, New York: pp. 92-99 (1989)).

In an embodiment, one could use the full length DNA. This DNA however need not be 100% identical to the DNA as depicted in SEQ ID NO 1. It is commonly known that when the overall identity of two full-length nucleic acids is at least 70%, these two nucleic acids may still encode the same protein. This phenomenon is commonly known as wobble in the second and especially the third base of each triplet encoding an amino acid. It is commonly accepted that when the identity on DNA level is at least 80% for the full length protein, proteins with a corresponding biological role are generally expressed. For obtaining a corresponding immunological response, it is preferred that the overall identity on DNA level is thus at least 80%, preferably at least 90%, more preferably 92%, even more preferably 94%, still even more preferably 96%, or even 98% up to 100% identity.

Another approach for assessing whether a nucleic acid is a nucleic acid for use according to the present invention is to assess whether this nucleic acid does hybridise under stringent conditions to a nucleic acid having the nucleotide sequence as depicted in SEQ ID NO: 1. If the nucleic acid hybridises under stringent conditions to the nucleotide sequence as depicted in SEQ ID NO: 1, it is considered to be a nucleic acid for use according to the invention. The definition of stringent conditions follows from the formula of Meinkoth and Wahl (1984. Hybridization of nucleic acids immobilized on solid supports. Anal. Biochem. 138: 267-284.)

$$Tm = [81.5° C. + 16.6(\log M) + 0.41(\% GC) - 0.61(\% \text{formamide}) - 500/L] - 1° C./1\% \text{ mismatch}$$

In this formula, M is molarity of monovalent cations; % GC is the percentage of guanosine and cytosine nucleotides in the DNA; L is the length of the hybrid in base pairs. Stringent conditions are those conditions under which nucleic acids or fragments thereof still hybridise, if they have a mismatch of 10% at the most, to the nucleic acid having the sequence depicted in SEQ ID NO: 1.

The present invention also pertains to antibodies against the protein for use according to the invention. It has been shown that these antibodies correspond to protection against an infection with the pathogenic micro organism that secrets this protein. Such antibodies could for example be used for treating an infection or for diagnostic purposes. Such antibodies may be polyclonal, monospecific or monoclonal (or derivatives thereof). If polyclonal antibodies are desired, techniques for producing and processing polyclonal sera are well-known in the art (e.g. Mayer and Walter, eds. *Immunochemical Methods in Cell and Molecular Biology*, Academic Press, London, 1987). Monoclonal antibodies, reactive against the polypeptide according to the invention (or variants or fragments thereof) according to the present invention, can be prepared by immunising inbred mice by techniques also known in the art (Kohler and Milstein, *Nature,* 256, 495-497, 1975). Methods for large-scale production of antibodies according to the invention are also known in the art. Such methods rely on the cloning of (fragments of) the genetic information encoding the protein according to the invention in a filamentous phage for phage display. Such techniques are described i.a. in review papers by Cortese, R. et al., (1994) in Trends Biotechn. 12: 262-267, by Clackson, T. & Wells, J. A. (1994) in Trends Biotechn. 12: 173-183, by Marks, J. D. et al., (1992) in J. Biol. Chem. 267: 16007-16010, by Winter, G. et al., (1994) in Annu. Rev. Immunol. 12: 433-455, and by Little, M. et al., (1994) Biotechn. Adv. 12: 539-555. The phages are subsequently used to screen camelid expression libraries expressing camelid heavy chain antibodies. (Muyldermans, S. and Lauwereys, M., Journ. Molec. Recogn. 12: 131-140 (1999) and Ghahroudi, M. A. et al., FEBS Letters 414: 512-526 (1997)). Cells from the library that express the desired antibodies can be replicated and subsequently be used for large scale expression of antibodies.

The invention will be further explained based on the following experimental results.

EXPERIMENTAL PROCEDURES

1 Culture Conditions

*S. parasitica* isolate CBS223.65 (C65), isolated from pike (*Esox lucius*), was obtained from the Centraal Bureau voor Schimmelcultures (CBS), The Netherlands and was grown routinely on Potato Dextrose Agar (Fluka) for 5 days at 18° C., before inoculation in pea broth and incubation for 2 days at 24° C. To accomplish *S. parasitica* sporulation, the mycelium was washed 3 times in sterile tap water and placed in a sterile 50:50 solution of demineralised water and aquarium tank water, obtained from regular fresh water aquaria. After overnight incubation, zoospores were collected. The *S. parasitica* strain used was grown under Scottish Executive Environment and Rural Affairs licence number PH/4/2009.

Rainbow trout weighing approximately 300 g were purchased from Almondbank, Perthshire, UK. Fish were maintained in 0.5 m³ flow-through, freshwater tanks (actual water volume 470 L) with a flow rate of approximately 5 L min$^{-1}$ at a temperature of 12° C. (+/−2° C.). The water quality was maintained with ammonia levels of less than 0.5 mg L$^{-1}$ and nitrite levels of less than 20 mg L$^{-1}$. All fish were fed ad libitum with commercial fish pellets (Ewos).

2 Infection of Trout with *S. parasitica*

Trout weighing ~30 g were transferred to the challenge room in 470 L tanks, with the water level adjusted to 150 L, one week prior to the challenge to allow acclimatisation. Feeding of the fish was stopped two days before the challenge. The water supply of each tank was isolated prior to the start of the challenge. Fish were put into a net (mesh size of 5 mm) and shaken in air for 2 min according to the Ami-momi technique (Hatai et al 1993; Stueland et al. 2005; both mentioned supra). The net containing the fish was dipped in a bucket of water to rinse off any mucus and the fish were released back into the challenge tank. A zoospore suspension of 3×10⁵ zoospores L$^{-1}$ was carefully added to each tank to minimise encystment. One unchallenged group who had undergone the Ami-momi treatment, but had no zoospore suspension added, served as the negative control. Two days post challenge the water flow was resumed to all tanks. Infected fish were recorded over the course of 14 days.

3 Sera Collection

Fish were anaesthetised in benzocaine (10 mg L$^{-1}$, Sigma) and approximately 400 μl of blood was harvested from the caudal vein using a 19 G needle. Blood samples were allowed to clot at 4° C. and centrifuged at 3000 g for 20 min to pellet the red blood cells. The supernatant was removed, aliquoted and stored at −20° C. for downstream applications.

4 Extraction of Proteins, and SDS-Polyacrylamide Gel Electrophoresis (PAGE)

S. parasitica strain C65 was grown for 2 days as described above. Culture filtrate was harvested, passed through a 70 μm cell strainer to remove any mycelia fragments, collected into a 50 ml Greiner tube and centrifuged at 1000 g. The supernatant was precipitated in 60% (v/v) acetone at −20° C. overnight. Secreted proteins were harvested by centrifugation at 13000 g for 10 min. A 0.3 ml aliquot of 2D lysis buffer (7.5 M urea, 2.5 M thiourea, 1.25 mM EDTA, pH 8.0, 625 mM DTT, 250 mM Tris-HCl, pH 10.8, 20% w/v Chaps, 50% v/v glycerol, 1X protease inhibitor (Roche) and 10% v/v carrier ampholytes (Bio-Lyte pH 4-6)) was used to resuspend each sample pellet. Samples underwent one-dimensional (1D) gel electrophoresis using NuPAGE® 12% Bis-Tris 1.0 mm, 10 or 15 well mini gels (Invitrogen). Protein samples were denatured for 3-5 min at 100° C., centrifuged for 15 s at 16200 g, and loaded on a 1-D gel, alongside 5 μl protein standard (New England Biolabs).

Approximately 50 μg protein was separated by isoelectric focusing of 7 cm Immobiline dry polyacrylamide gel strips with an immobilized pH 3-11 NL (non-linear) gradient (Amersham Biosciences) using an IPGphor (Amersham Biosciences). Strips were focused for a total of 8000 V/h. Proteins were separated in the second dimension on Novex NuPAGE 12% Bis-Tris mini-gels (Invitrogen) according to the manufacturer's recommendations. Gels were stained using the colloidal Coomassie based GelCode Blue Stain Reagent (Pierce) according to the manufacturer's protocol.

5 Immunoblotting

The gels run as described above were transferred to nitrocellulose membranes. Each membrane was incubated at 4° C. overnight in PBS+0.2% Tween-20 (PBS-T) and then for 1 hr in PBS-T+10% skimmed milk powder (MPBS-T). After washing the membrane several times with PBS-T, it was incubated for 2 hr with rainbow trout sera diluted 1:100 in PBS-T. Each membrane was washed several times, followed by incubation with HRP-conjugated anti-trout/anti-salmon IgM antibody (Aquatic Diagnostics Ltd, Stirling) diluted 1:54 in MPBS-T as recommended by the manufacturer. After several washes, membranes were developed by Pierce ECL Western Blotting Substrate (Thermo Scientific), according to manufacturer's protocol. Membranes were exposed to Kodak BioMax XAR film (GE Healthcare).

6 Sample Preparation for LC-MS/MS

Protein spots identified by Immunoblotting were excised from the gel and digested with trypsin (sequencing grade, modified; Promega) using an Investigator ProGest robotic workstation (Genomic Solutions Ltd.). Briefly, proteins were reduced with 10 mM Dithiothreitol (DTT) (60° C., 20 min), S-alkylated with 50 mM iodoacetamide (25° C., 10 min) then digested with trypsin (37° C., 8 h). The resulting tryptic peptide extract was dried by rotary evaporation (SC110 SpeedVac; Savant Instruments) and dissolved in 0.1% formic acid for LC-MS/MS analysis.

7 MS/MS Analysis

Peptide solutions were analysed using an HCTultra PTM Discovery System 3D ion trap (Bruker Daltonics Ltd.) coupled to an UltiMate 3000 LC System, (Dionex (UK) Ltd.). Peptides were separated on a Monolithic Capillary Column (200 μm i.d.×5 cm; Dionex) at a flow rate of 2.5 μL/min using a gradient of acetonitrile (6-38% over 12 min) in 0.04% (aq.) formic acid. Peptide fragment mass spectra were acquired in data-dependent AutoMS(2) mode with a scan range of 300-1500 m/z, three averages, and up to three precursor ions selected from the MS scan (100-2200 m/z). Precursors were actively excluded within a 1.0 min window, and all singly-charged ions were excluded, since our machine does not pick these up. Peptide peaks were detected and deconvoluted automatically using DataAnalysis software (Bruker). Mass lists in the form of Mascot Generic Files were created automatically and used as the input for Mascot MS/MS Ions searches of the S. parasitica predicted protein database (downloaded from the Broad institute website) using the Matrix Science web server (available from the website of Matrix Science). The default search parameters used were: enzyme=trypsin; max missed cleavages=1; fixed modifications=carbamidomethyl (C); variable modifications=oxidation (M); peptide tolerance±1.5 Da; MS/MS tolerance±0.5 Da; peptide charge=2+ and 3+; instrument=ESI-TRAP.

Results

1 Infection of Trout with S. parasitica

Following the addition of zoospores, trout were monitored for the development of symptoms consistent with saprolegniosis. None of the trout, however, displayed symptoms of successful infection. Apparently these trout were completely protected against infection with the pathogenic parasite. Blood was harvested from the trout 14 days after the addition of zoospores for investigation of the trout response to the challenge.

2 Recognition of Secreted Proteins by Trout Sera

Three independent biological replicates of secreted proteins from S. parasitica strain C65 were harvested and electrophoresed as described. On a 1D gel, despite the presence of a wealth of proteins, only one band of around 40 kDa appeared to be recognised by the rainbow trout sera on the Western blot. The corresponding material was excised from the stained gels, digested with trypsin and the solubilised material was analysed by LC-MS/MS.

3 Protein Identification

Obtained MS/MS data were compared with an in silico digest of the S. parasitica proteome, using Mascot, with a high confidence limit setting (P<0.05). The corresponding protein sequence is depicted as SEQ ID No 2. The coding DNA is depicted as SEQ ID No 1. The protein was identified as SPRG_14567 in the genome data base of S. parasitica on the basis of ion score and sequence coverage as predicted by Mascot MS/MS Ions searches of the S. parasitica predicted protein database. The found protein has significant sequence similarity to a family of 29 other S. parasitica proteins, 11 Phytophthora infestans proteins, 9 Phytophthora sojae proteins and 7 Phytophthora ramorum proteins. Of the S. parasitica proteins, 24, including SPRG_14567, contain the subtilase domain while 10 of the 11 P. infestans hits belong to the subtilase family.

With the protein sequence, BlastP was performed against the NCBI conserved domain database (CDD) as mentioned by Marchler-Bauer et al. in *Nucleic acids research* 35, 2007. This showed that the protein has also significant sequence similarity to serine proteases from a range of oomycetes (including P. infestans, Aphanomyces astaci, Lagenidium giganteum and Pythium carolinianum) and bacteria (including Micromonospora aurantiaca, Salinispora sp., Streptosporangium roseum, Streptomyces sp. and Beutenbergia cavernae). The sequence was analysed for the presence of a signal peptide and transmembrane domains. Only a signal peptide was identified, suggesting that the protein is secreted, therefore the protein is tentatively named SpSsp1 (S. parasitica secreted serine protease 1). NetNGlyc reported positive results for the amino acid sequence of SpSsp1, with a predicted N-glycosylation site on reside 231 (potential: 0.69; jury agreement: 9/9). A second N-linked glycosylation site is predicted on residue 434, however the potential and jury agreement for this site are low and may represent a false positive (0.51 and 5/9, respectively). Analysis of the predicted protein sequence for the presence of conserved domains revealed the presence of the Peptidases_S8_S53 superfamily domain (E value $2.2e^{-38}$) with the conserved Asp/His/Ser catalytic triad (indicated in FIG. 2A). Analysis by InterProScan confirmed the presence of the superfamily domain predicted by the NCBI conserved domain database mentioned supra.

The invention claimed is:

1. A vaccine for protecting salmonids against infection with a *Saprolegnia parasitica* comprising a subtilisin-like serine protease; wherein the protease has an amino acid sequence that is at least 90% identical to SEQ ID NO 2, and an adjuvant; wherein the adjuvant amplifies one or more particular processes in the cascade of immunological events.

2. The vaccine of claim 1 that further comprises a pharmaceutically acceptable carrier.

3. The vaccine of claim 2, that further comprises an antigen of one or more micro-organisms selected from the group consisting of *Aeromonas salmonicida, Yersinia ruckeri, Flavobacterium columnarae, Flavobacterium psychrophilum, Vibrio ordalii, Vibrio anguillarum, Vibrio salmonicida, Moritella viscose,* infectious pancreatic necrosis virus (IPNV), salmonid alphavirus (SAV), infectious hematopoietic necrosis virus IHNV), viral haemorrhagic septicaemia virus (VHSV) and infectious salmon anaemia virus (ISAV).

4. The vaccine of claim 1, that further comprises an antigen of one or more micro-organisms selected from the group consisting of *Aeromonas salmonicida, Yersinia ruckeri, Flavobacterium columnarae, Flavobacterium psychrophilum, Vibrio ordalii, Vibrio anguillarum, Vibrio salmonicida, Moritella viscose,* infectious pancreatic necrosis virus (IPNV), salmonid alphavirus (SAV), infectious hematopoietic necrosis virus IHNV), viral haemorrhagic septicaemia virus (VHSV) and infectious salmon anaemia virus (ISAV).

5. A live recombinant carrier (LRC) comprising a DNA that encodes a subtilisin-like serine protease; wherein said subtilisin-like serine protease has an amino acid sequence that is at least 70% identical to SEQ ID NO 2.

6. The LRC of claim 5 wherein the DNA encodes a subtilisin-like serine protease; wherein the amino acid sequence of said subtilisin-like serine protease is at least 90% identical to SEQ ID NO 2.

7. The LRC of claim 5 wherein the DNA comprises a nucleotide sequence that is at least 70% identical to the nucleotide sequence of SEQ ID NO 1.

8. A vaccine for protecting salmonids against infection with a *Saprolegnia* species comprising the LRC of claim 7.

9. A vaccine for protecting salmonids against infection with a *Saprolegnia* species comprising the LRC of claim 6.

10. A vaccine for protecting salmonids against infection with a *Saprolegnia* species comprising the LRC of claim 5.

11. A vaccine for protecting salmonids against infection with a *Saprolegnia parasitica* comprising a subtilisin-like serine protease; wherein the protease has an amino acid sequence that is at least 96% identical to SEQ ID NO 2, and an adjuvant; wherein the adjuvant amplifies one or more particular process in the cascade of immunological events.

12. The vaccine of claim 11 that further comprises a pharmaceutically acceptable carrier.

13. The vaccine of claim 12, that further comprises an antigen of one or more micro-organisms selected from the group consisting of *Aeromonas salmonicida, Yersinia ruckeri, Flavobacterium columnarae, Flavobacterium psychrophilum, Vibrio ordalii, Vibrio anguillarum, Vibrio salmonicida, Moritella viscose,* infectious pancreatic necrosis virus (IPNV), salmonid alphavirus (SAV), infectious hematopoietic necrosis virus IHNV), viral haemorrhagic septicaemia virus (VHSV) and infectious salmon anaemia virus (ISAV).

* * * * *